United States Patent [19]

ter Haken et al.

[11] Patent Number: 4,532,329
[45] Date of Patent: Jul. 30, 1985

[54] 3-(R-THIO)PROPIONIC ACID SUBSTITUTED ON ADJACENT CARBON ATOMS BY PYRIDYL AND OPTIONALLY-SUBSTITUTED PHENYL, AND CORRESPONDING OPTIONALLY-SUBSTITUTED ALKYL ESTERS

[75] Inventors: Pieter T. Haken, Eastling, Nr. Faversham; Shirley B. Webb, Faversham, both of England

[73] Assignee: Shell Oil Company, Houston, Tex.

[21] Appl. No.: 535,461

[22] Filed: Sep. 26, 1983

[30] Foreign Application Priority Data

Sep. 27, 1982 [GB] United Kingdom ............... 8227481

[51] Int. Cl.³ .......................................... C07D 213/32
[52] U.S. Cl. .................................. 546/342; 546/330; 546/335
[58] Field of Search ............... 546/342, 330, 334, 335, 546/336, 344, 339

[56] References Cited

U.S. PATENT DOCUMENTS 3,397,273  8/1968  Van Heyningen et al. ........ 546/342

OTHER PUBLICATIONS

Mondeshka et al., CA, 85:5460q, vol. 85.
Fisnerova et al., CA, 85:46150g.

Primary Examiner—Jane T. Fan

[57] ABSTRACT

Novel compounds of the formula

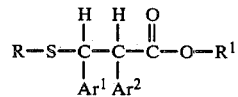

wherein one of $Ar^1$ and $Ar^2$ is pyridyl and the other is optionally substituted phenyl, R is optionally substituted alkyl and $R^1$ is hydrogen or optionally substituted alkyl, and salts thereof, useful as fungicides.

3 Claims, No Drawings

3-(R-THIO)PROPIONIC ACID SUBSTITUTED ON ADJACENT CARBON ATOMS BY PYRIDYL AND OPTIONALLY-SUBSTITUTED PHENYL, AND CORRESPONDING OPTIONALLY-SUBSTITUTED ALKYL ESTERS

The present invention relates to fungicidally active compounds.

Certain alkane derivatives have been disclosed as fungicides, for example see U.S. Pat. No. 3,397,273. The applicants have now found that certain novel ethane derivatives also have useful fungicidal activity.

The present invention therefore provides a compound of the general formula (I)

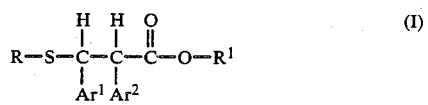

wherein one of $Ar^1$ and $Ar^2$ is pyridyl and the other is optionally substituted phenyl, R contains up to eight carbon atoms and is optionally substituted alkyl, $R^1$ is hydrogen or contains up to six carbon atoms and is optionally substituted alkyl, and salts and metal complexes thereof.

Throughout this specification, unless otherwise stated, any aliphatic moiety present preferably contains up to 6, especially up to 4, carbon atoms.

Suitable substituents which may be present in an optionally substituted aliphatic group include halogen atoms, alkoxy, alkylthio, cyano, carboxy, alkoxycarbonyl, acetyloxy, formyloxy, hydroxy, amino and cycloalkyl groups and optionally substituted phenyl or phenoxy groups. Suitable substituents which may be present in an optionally substituted phenyl or phenoxy group include halogen atoms, hydroxy, methylenedioxy, amio, cyano, alkylsulphonyl and nitro groups and optionally substituted alkyl, alkenyl, alkynyl, alkoxy, alkylthio, alkoxycarbonyl, phenyl and phenoxy groups.

A phenyl group $Ar^1$ or $Ar^2$ is preferably unsubstituted or substituted by up to 3 of the same or different substituents given above. Most preferably it is unsubstituted, monosubstituted or disubstituted. Preferred substituents are selected from halogen atoms and nitro, cyano, alkyl, haloalkyl, alkoxy, haloalkoxy and alkylthio groups. Especially preferred substituents are 1 or 2 halogen atoms.

Preferred compounds of the general formula I and salts and complexes thereof, are those in which the phenyl group is substituted by halogen, for example a mono or di-chloro or fluoro substituted phenyl group, preferably a dichloro substituted phenyl group.

As stated above, the invention includes metal salt complexes and salts of compounds of the general formula I. Suitable salts include salts with sulphonic acids, for example benzene- or toluenesulphonic acid, carboxylic acids for example tartaric or acetic acid, or inorganic acids for example the hydrohalic acids or sulphuric acid. The salt may be a metal salt, for example an alkali or alkaline earth metal salt, the ammonium salt, or a substituted ammonium salt, for example an alkyl-substituted ammonium salt. Suitable metal salts which form complexes with compounds of the general formula I include those of heavy metals such as iron, copper, zinc and manganese, in which the anions may, for example, be derived from one of those acids given above.

It will be appreciated that both carbon atoms of the ethane base unit are asymmetric and give rise to isomeric forms of compounds of general formula I. Other possibilities for isomerism may arise depending on the specific groups present in the molecule. The invention encompasses all individual isomers as well as mixtures of isomers.

The invention further provides a process for the preparation of a compound according to the invention, which comprises reacting a compound of the general formula

with a compound of the general formula HR.

In general, the process according to the invention leads to a mixture of isomers of the compound of general formula I. As noted above both carbon atoms of the ethane base unit are asymmetric. This asymmetry alone gives rise to various different sterioisomers whose absolute configuration may be defined in terms of the Cahn-Ingold-Prelog convention [see Roberts and Caserio, Basic Principles of Organic Chemistry, p. 529, (1965)]. Using this convention, isomers RR and SS are enantiomorphs with identical physical properties which usually prevents separation by physical methods; similarly for the isomers RS and SR.

However, the isomers RR and RS are diastereoisomers with different physical properties which enable separation by conventional means; this is also the case for the isomers SS and SR.

Furthermore as noted above, other possibilities for isomerism may arise depending on the specific groups present in the molecule. These isomers may also differ in their physical properties.

Hence, certain of the reaction products may be separated by conventional physical means, for example using chromatography. When separating a mixture of two isomer pairs, one isomer pair will usually be eluted faster than the other pair.

The molar ratio of the reactants used in the process according to the invention is not critical and may for example be in the range of from 5:1 to 1:5, especially 2:1 to 1:2.

The reaction is suitably carried out in the presence of a solvent; typical solvents are for example alcohols such as methanol or ethanol; ethers such as tetrahydrofuran or dimethoxyethane; chlorinated hydrocarbons such as methylene chloride; esters such as ethyl acetate; amides such as dimethylformamide or dimethyl acetamide; ketones such as acetone, dimethyl ketone or methyl ethyl ketone; and nitroalkanes such as nitromethane. Mixtures of solvents may be suitable.

The reaction is preferably carried out in the presence of a base. Suitable basis include primary, secondary or tertiary amines, for example triethylamine or the secondary cyclic amine piperidine; alkali metal hydrides, amides or alkoxides, for example sodium ethoxide; and alkali metal and alkaline earth metal hydroxides.

The reaction is preferably carried out in an inert atmosphere, for example under nitrogen, especially when R contains a sulphur atom.

The temperature of the reaction is suitably in the range of from 0° to 180° C. It may in some cases be convenient to carry out the reaction at the reflux temperature of the reaction mixture.

A resulting compound of formula I may be converted into a salt or a metal salt complex thereof by methods analogous to known methods, for example by reaction with an oxidising agent or with the appropriate acid, base or salt. A resulting salt can be converted into the free compound by reaction with an acid binding agent or an acid, as appropriate.

The starting material of the general formula II may be prepared by reacting a compound of the general formula III

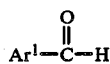
(III)

with a compound of general formula (IV)

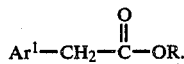
(IV)

The conditions under which this reaction may be carried out are described in our copending application Ser. No. 535,496.

The compounds of the invention have been found to show interesting activity as fungicides. Accordingly the invention provides a fungicidal composition comprising a compound of the general formula I as defined above or an N-oxide, salt or metal salt complex thereof in association with at least one carrier and a method of making such a composition which comprises bringing a compound of general formula I as defined above or an N-oxide, salt or metal salt complex into association with at least one carrier.

The invention further provides a method of controlling fungus at a locus, which comprises applying to the locus a compound or a composition according to the invention. Suitable dosages are, for example, in the range of from 0.05 to 4 kg active material per hectare. The method of the invention is especially useful for the treatment or prevention of fungal attack in seeds, soil or plants; crops susceptible to powdery mildews, for example cereals or apples, may for example be treated.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins; for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3-10% w of a dispersing agent and, where necessary, 0-10% w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½-10% w of active ingredient. Granules are usually prepared to have a size between 10 and 100 BS mesh (1.676-0.152 mm), and may be manufactured by agglomeration or impregnation techniques. Generally, granules will contain ½-75% w active ingredient and 0-10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10-50% w/v active ingredient, 2-20% w/v emulsifiers and 0-20% w/v of other additives such as stabilisers, penetrants and corrosion inhibitors. Suspension concentrates are usually compounded so as to obtain a stable, no-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formation to assist in preventing sedimentation or as anti-freeze agents for water.

Aqueous dispersions and emulsions, for example compositions obtained by diluting a wettable powder or a concentrate according to the invention with water, also lie within the scope of the present invention. The said emulsions may be of the water-in-oil or of the oil-in-water type, and may have a thick 'mayonnaise'-like consistency.

The composition of the invention may also contain other ingredients, for example, other compounds possessing herbicidal, insecticidal or fungicidal properties.

The following Examples illustrate the invention. The terms "A", "B" and "C" refer to the order in which the isomeric reaction products are eluted from the chromatography column, "A" refering to the product eluted first etc.

EXAMPLE 1

Preparation of methyl 2-(2',4'-dichlorophenyl)-3-(1'-methyl propylthio)-3-(3-pyridyl)propanoic ester To a stirred solution of methyl 2-(2',4'-dichlorophenyl)-3-(3-pyridyl)propenoic ester (5.7 g) in dry dimethoxyethane (50 ml) and dry methanol (10 ml) under a nitrogen atmosphere was added 1-methylpropane-1-thiol (16.6 g) and piperidine (1.57 g). The mixture was stirred and heated under reflux for 16 hours. After cooling, solvents were removed in vacuo, and the residue taken up in ether, washed three times with water and dried with magnesium sulphate. After filtration and removal of the solvent, the residual oil was subjected to column chromatography on silica gel, eluting with ether/hexane (2:1).

Two fractions were eluted. The faster eluted material (A) was obtained in 46% yield as a white solid, melting point 81°–82.5° C. The slower eluted material (B) was obtained in a 28% yield as a white solid, melting point 86°–91° C.

The following elemental analysis results were obtained:

Product A Calculated: C: 57.29; H: 5.28; N: 3.52; Found: C: 57.3; H: 5.3; N: 3.4.

Product B Calculated: C: 57.29; H: 5.28; N: 3.52; Found: C: 57.5; H: 5.6; N: 3.6.

EXAMPLE 2

Preparation of the HCl salt of the product A of Example 1

Hydrogen chloride gas was bubbled into a stirred solution of product A of Example 1 (1.0 g) in dry ether (25 ml) for about 5 minutes. Nitrogen was then bubbled through the reaction mixture to remove excess hydrogen chloride. The white solid that had separated was filtered off, washed with ether followed by 40/60 petroleum spirit, and dried.

The yield of product was 1.1 g (100%); melting point 177°–181° C.

The following elemental analysis results were obtained:

Calculated: C: 52.47; H: 5.06; N: 3.22; Found: C: 52.6; H: 5.5; N: 3.2.

EXAMPLES 3 TO 13

By methods analogous to those described in Examples 1 and 2, the following compounds were prepared. Analysis and physical data figures are given in Table I.

TABLE I

| Example No. | Ar¹ | Ar² | R | R¹ | | Elemental Analysis | | | Physical Data |
|---|---|---|---|---|---|---|---|---|---|
| | | | | | | C | H | N | |
| 3A | 3-pyridyl | 2,4-dichlorophenyl | EtO—C(=O)—CH₂— | —CH₃ | Calc. Found | 53.27 53.2 | 4.44 4.4 | 3.27 3.3 | Mpt: 67–69° C. |
| 3B | 3-pyridyl | 2,4-dichlorophenyl | EtO—C(=O)—CH₂— | —CH₃ | Calc. Found | 53.27 53.1 | 4.44 4.6 | 3.27 3.3 | Mpt: 77–78° C. |
| 4* copper (II) chloride complex (2 moles of ethane derivative per mole of CuCl₂) | 3-pyridyl | 2,4-dichlorophenyl | EtO—C(=O)—CH₂— | —CH₃ | Calc. Found | 46.04 45.7 | 3.84 3.9 | 2.83 2.8 | Mpt: 153–154° C. (with decomposition) |
| 5A | 3-pyridyl | 2,4-dichlorophenyl | (CH₃)₃C— | —CH₃ | Calc. Found | 57.29 57.3 | 5.28 5.3 | 3.52 3.6 | Mpt:127–129° C. |
| 5B | 3-pyridyl | 2,4-dichlorophenyl | (CH₃)₃C— | —CH₃ | Calc. Found | 57.29 56.8 | 5.28 5.1 | 3.52 3.6 | Mpt: 106–112° C. |
| 6A | 3-pyridyl | 2,4-dichlorophenyl | (CH₃)₃C— | —(CH₂)₃CH₃ | Calc. Found | 60.00 60.1 | 6.14 6.2 | 3.18 3.3 | Mpt: 79–81° C. |
| 6B | 3-pyridyl | 2,4-dichlorophenyl | (CH₃)₃C— | —(CH₂)₃CH₃ | Calc. Found | 60.00 60.1 | 6.14 6.4 | 3.18 3.2 | Mpt: 104–106° C. |
| 7A | 2,4-dichlorophenyl | 3-pyridyl | (CH₃)₃C— | —(CH₂)₃CH₃ | Calc. Found | 60.00 59.6 | 6.14 6.2 | 3.18 3.0 | Mpt: 73–75° C. |
| 7B | 2,4-dichlorophenyl | 3-pyridyl | (CH₃)₃C— | —(CH₂)₃CH₃ | Calc. Found | 60.00 59.8 | 6.14 6.2 | 3.18 3.3 | Mpt: 92.5–93.5° C. |
| 8A | 3-pyridyl | 2,4-dichlorophenyl | HO—CH₂CH₂— | —CH₃ | Calc. | 52.85 | 4.40 | 3.63 | Mpt: 143–149° C. |

TABLE I-continued

| Example No. | $Ar^1$ | $Ar^2$ | R | $R^1$ | | Elemental Analysis C | H | N | Physical Data |
|---|---|---|---|---|---|---|---|---|---|
| 8B | 3-pyridyl | 2,4-dichlorophenyl | $HO-CH_2CH_2-$ | $-CH_3$ | Found Calc. Found | 52.5 52.85 52.4 | 4.1 4.40 4.5 | 3.1 3.63 3.6 | |
| 9A | 3-pyridyl | 2,4-dichlorophenyl | $\underset{CH_3-CH-}{Ph}$ | $-CH_3$ | Calc. Found | 61.88 61.5 | 4.71 4.7 | 3.14 3.1 | Mpt: 94–100° C. |
| 9B | 3-pyridyl | 2,4-dichlorophenyl | $\underset{CH_3-CH-}{Ph}$ | $-CH_3$ | Calc. Found | 61.88 62.8 | 4.71 5.3 | 3.14 3.0 | Mpt: 64–76° C. |
| 9C | 3-pyridyl | 2,4-dichlorophenyl | $\underset{CH_3-CH-}{Ph}$ | $-CH_3$ | Calc. Found | 61.88 62.0 | 4.71 4.7 | 3.14 3.1 | Mpt: 107–109° C. |
| 10 | 2,4-dichlorophenyl | 3-pyridyl | $(CH_3)_3C-$ | $-CH_3$ | Calc. Found | 57.29 56.7 | 5.28 5.3 | 3.52 3.4 | oil |
| 11A | 3-pyridyl | 2,4-dichlorophenyl | $CH_3COCH_2CH_2-$ | $-CH_3$ | Calc. Found | 53.27 53.1 | 4.44 4.6 | 3.27 3.6 | Mpt: 83–85° C. |
| 11B | 3-pyridyl | 2,4-dichlorophenyl | $CH_3COCH_2CH_2-$ | $-CH_3$ | Calc. Found | 53.27 53.1 | 4.44 4.7 | 3.27 3.2 | oil |
| 12 | 3-pyridyl | 2,4-dichlorophenyl | $ClCH_2CH_2-$ | $-CH_3$ | Calc. Found | 50.43 50.3 | 3.96 4.0 | 3.4 3.4 | Mpt: 84–86° C. |
| 13 | 3-pyridyl | 2,4-dichlorophenyl | $HCOCH_2CH_2-$ | $-CH_3$ | Calc. Found | 52.17 52.2 | 4.11 4.2 | 3.38 3.3 | Mpt: 79–83 |

EXAMPLE 14

(a) Activity against vine downy mildew (*Plasmopara viticola*; Pv.t)

The test is a translaminar protectant one using a foliar spray. The upper surfaces of leaves of whole vine plants are sprayed using a moving track sprayer. The track sprayer delivers 620 l/ha and the concentration of active material is calculated to give an application rate of 1 kg/ha. The lower surfaces of the leaves are then inoculated, up to 6 hours after treatment with the test compound, by spraying with an aqueous suspension containing $10^5$ zoosporangia/ml. The inoculated plants are kept for 24 hours in a high humidity compartment, 4 days at glasshouse ambient temperature and humidity and then returned for a further 24 hours to high humidity. Assessment is based on the percentage of leaf area covered by sporulation compared with that on control leaves.

(b) Activity against vine grey mould (*Botrytis cinerea*; B.c.)

The test is a direct eradicant one using a foliar spray. The under-surface of the detached vine leaves are inoculated by pipetting ten large drops of an aqueous suspension containing $5 \times 10^5$ conidia/ml on to them. The inoculated leaves kept uncovered overnight during which time the fungus has penetrated the leaf and a visible necrotic lesion may be apparent where the drop was made. The infected regions are sprayed directly with a dosage of 1 kg of active material per hectare using a track sprayer as described under (a). When the spray has dried the leaves are covered with a petri dish and the disease allowed to develop under these humid conditions. The extent of the necrotic lesion beyond the original drop together with the degree of sporulation is compared with that on control leaves.

(c) Activity against potato late blight (*Phytophora infestans*; P.i.p.)

The test measures the direct protectant activity of compounds applied as a foliar spray. Tomato plants, cultivar Ailsa Craig, 1–15 cms high, in monopots are used. The whole plant is sprayed at a dosage of 1 kilogram of active material per hectare using a track sprayer. The plant is then inoculated up to 6 hours after treatment with the test compound, by spraying with an aqueous suspension containing $5 \times 10^3$ zoosporangia/ml. The inoculated plants are kept in high humidity for 3 days. Assessment is based on comparison between the levels of disease on the treated and control plants.

(d) Activity against barley powdery mildew (*Erysiphe graminis*; E.g.)

The test measures the direct antisporulant activity of compounds applied as a foliar spray. For each compound about 40 barley seedlings are grown to the one-leaf stage in a plastic pot of sterile potting compost. Inoculation is effected by dusting the leaves with conidia of Erysiphe graminis, spp. hordei. 24 hours after inoculation the seedlings are sprayed with a solution of the compound in a mixture of acetone (50%), surfactant (0.04%) and water using a track sprayer as described under (a). The rate of application is equivalent to 1 kg of active material per hectare. Assessment of disease is made 5 days after treatment, when the overall level of sporulation on the treated plants is compared with that on control plants.

(e) Activity against apple powdery mildew
(*Podsophaera leucotrica;* P.l.)

The test is a direct anti-sporulant one using a foliar spray. The upper surfaces of leaves of whole apple seedlings are inoculated by spraying with an aqueous suspension containing $10^5$ conidia/ml 2 days prior to treatment with the test compound. The inoculated plants are immediately dried and kept at glasshouse ambient temperatures and humidity prior to treatment. The plants are sprayed at a dosage of 1 kilogram of active material per hectare using a track sprayer. After drying the plants are returned to a compartment at ambient temperature and humidity for up to 9 days, followed by assessment. Assessment is based on the percentage of the leaf area covered by sporulation compared with that on leaves of control plants.

(f) Activity against peanut leaf spot (*Cercospora arachidicola;* Ca)

The test is a direct eradicant one using a foliar spray. The upper surfaces of the leaves of peanut plants (12-20 cms high, monopots) are inoculated by spraying with an aqueous suspension containing $10^5$ conidia/ml 4 hours prior to treatment with the test compound. The inoculated plants are kept at high humidity and then allowed to dry before treatment by spraying at a dosage of 1 kg of active material per hectare using a track sprayer. After spraying the plants are moved to a humid compartment at 25°-28° C. for a further period of up to 10 days. Assessment is based on a comparison between the levels of disease on the treated and control plants.

The extent of disease control achieved in these tests is expressed as a control rating in Table II below; greater than 80% disease control is given the rating 2 after the test; control of between 50 and 80% is given the rating 1 after the test.

TABLE II

| Compound of Example No. | Greater than 50% disease control achieved in the below indicated tests |
|---|---|
| 1A | Pip (1) Eg (2) Pl (2) |
| 1B | Bc (1) Eg (2) Pl (1) |
| 2 | Pip (1) Pl (2) Ca (1) |
| 3A | Bc (1) Pip (1) Eg (2) |
| 3B | Pip (1) Eg (2) |

TABLE II-continued

| Compound of Example No. | Greater than 50% disease control achieved in the below indicated tests |
|---|---|
| 4 | Pvt (1) Pip (1) Pl (2) |
| 5A | Eg (2) Pl (1) |
| 5B | Eg (2) |
| 6A | Pl (2) |
| 6B | Pl (2) |
| 7A | Eg (1) |
| 7B | Eg (1) |
| 8A | Eg (2) |
| 8B | Eg (2) Pl (1) |
| 9A | Eg (2) Pl (2) |
| 9B | Eg (2) |
| 9C | Eg (2) |
| 10 | Pvt (1) Bc (1) Eg (2) Pl (2) Pip (1) |
| 11A | Eg (1) Pl (2) |
| 11B | Pl (2) |
| 12 | Pvt (1) Bc (1) Eg (1) Pl (2) |
| 13 | Eg (1) Pl (2) |

We claim:

1. A compound of the formula:

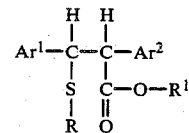

wherein one of $Ar^1$ and $Ar^2$ is pyridyl, and the other is phenyl or phenyl substituted by from one to three halogen atoms; R contains from one to eight carbon atoms and is alkyl, haloalkyl, alkoxyalkyl, alkylthioalkyl, cyanoalkyl, carboxyalkyl, alkoxycarbony alkyl acetyloxyalkyl, formyloxyalkyl, hydroxyalkyl, aminoalkyl, cycloalkylalkyl, phenalkyl or phenoxyalkyl; $R^1$ is hydrogen or alkyl of from one to eight carbon atoms; a salt thereof with a sulfonic acid, a carboxylic acid, a hydrohalic acid, sulfuric acid, an alkali metal, an alkaline earth metal, ammonium, an alkyl-substituted ammonium, and a complex thereof with iron, copper, zinc or manganese salt of the acids described above.

2. A compound according to claim 1 wherein the phenyl group $Ar^1$ or $Ar^2$ is substituted by one or two chlorine atoms.

3. A compound according to claim 2 wherein R is alkyl, haloalkyl, hydroxyalkyl, alkoxycarbonylalkyl, acetyloxyalkyl, formyloxyalkyl or alkyl substituted on the alpha carbon atom by phenyl.

* * * * *